(12) United States Patent
Ning et al.

(10) Patent No.: US 10,636,524 B2
(45) Date of Patent: Apr. 28, 2020

(54) METHOD AND SYSTEM FOR OPTIMIZED WAKE-UP STRATEGY VIA SLEEPING STAGE PREDICTION WITH RECURRENT NEURAL NETWORKS

(71) Applicant: TCL RESEARCH AMERICA INC., San Jose, CA (US)

(72) Inventors: Guanghan Ning, San Jose, CA (US); Haohong Wang, San Jose, CA (US); Xiaobo Ren, San Jose, CA (US)

(73) Assignee: TCL RESEARCH AMERICA INC., San Jose, CA (US)

( * ) Notice: Subject to any disclaimer, the term of this patent is extended or adjusted under 35 U.S.C. 154(b) by 828 days.

(21) Appl. No.: 15/248,639

(22) Filed: Aug. 26, 2016

(65) Prior Publication Data

US 2018/0060507 A1  Mar. 1, 2018

(51) Int. Cl.
```
G16H 50/20      (2018.01)
A61B 5/00       (2006.01)
A61M 21/00      (2006.01)
A61B 5/11       (2006.01)
G16H 50/30      (2018.01)
G16H 50/50      (2018.01)
G16H 40/63      (2018.01)
A61B 5/0205     (2006.01)
```

(52) U.S. Cl.
CPC .......... *G16H 50/20* (2018.01); *A61B 5/0205* (2013.01); *A61B 5/11* (2013.01); *A61B 5/4812* (2013.01); *A61B 5/6898* (2013.01); *A61B 5/7246* (2013.01); *A61B 5/7264* (2013.01); *A61M 21/00* (2013.01); *G16H 40/63* (2018.01); *G16H 50/30* (2018.01); *G16H 50/50* (2018.01); *A61M 2021/0022* (2013.01); *A61M 2021/0027* (2013.01); *A61M 2021/0083* (2013.01); *A61M 2205/505* (2013.01); *A61M 2230/04* (2013.01); *A61M 2230/40* (2013.01); *A61M 2230/63* (2013.01)

(58) Field of Classification Search
CPC ........ G16H 50/20; G16H 50/50; G16H 40/63; A61B 5/0205; A61B 5/11
USPC ........ 600/300–301, 372, 382–384, 386–394, 600/529, 544–545; 705/2–3
See application file for complete search history.

(56) References Cited

U.S. PATENT DOCUMENTS

2010/0099954 A1* 4/2010 Dickinson ............ A61B 5/0006
600/300

* cited by examiner

*Primary Examiner* — Daryl C Pope
(74) *Attorney, Agent, or Firm* — Anova Law Group, PLLC (57) ABSTRACT

A method for optimized wake-up strategy via sleeping stage prediction with recurrent neural networks is provided. The method comprises receiving a set of raw sensory data of a user's sleeping status; translating the set of raw sensory data into a plurality of sleeping stages; saving the plurality of sleeping stages as a history of sleeping stages; determining a current sleeping stage; predicting a plurality of future sleeping stages of the user in an upcoming interval; calculating a wakeup score of the current sleeping stage and a wakeup score of each future sleeping stage; determining an optimized sleeping stage for wake up based on the wakeup score through comparing the wakeup score of the current sleeping stage and the wakeup scores of the future sleeping stages; and triggering an alarm impulse to wake up the user at the optimized sleeping stage for wake up.

20 Claims, 6 Drawing Sheets

METHOD AND SYSTEM FOR OPTIMIZED WAKE-UP STRATEGY VIA SLEEPING STAGE PREDICTION WITH RECURRENT NEURAL NETWORKS

FIELD OF THE INVENTION

The present invention relates generally to the field of computer technologies and, more particularly, to a method and system for optimized wake-up strategy via sleeping stage prediction with recurrent neural networks.

BACKGROUND

Sleep is a very important part of human's daily life, and sleep quality has a great impact on various aspects of one's metal and physical status, such as one's fatigue, mood, attention, and concentration, etc. High quality sleep can make a big difference in one's quality of life. Therefore, various instruments for evaluating sleep quality are emerging.

Figure 1:
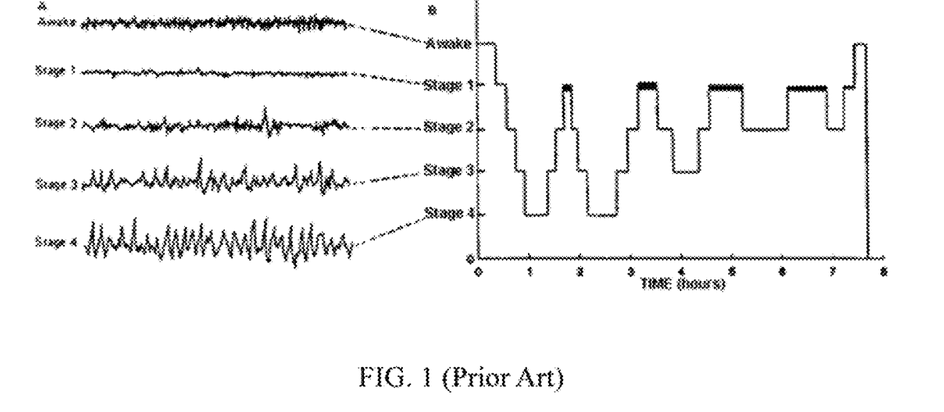
FIG. 1 illustrates typical raw sensory data and corresponding sleeping stages.

People often experience two different phases of sleeps during the night: Rapid Eye Movement (REM) sleep and non-REM sleep, which may alternately appear through the night. The periodical rhythm of the REM and the non-REM sleeps are called a sleep cycle. Non-REM sleep can be subdivided into 4 sub-stages, in which each successive stage of non-REM sleep is indicative of a deeper sleep, with stage 1 as the lightest and stage 4 as the deepest. FIG. 1 illustrates a typical person's sleeping stages through the night.

Polysomnography, which allows an evaluation of the sleep stages (Wake, REM, Non-REM) for identifying various forms of sleep disorders, remains a gold standard for sleep quality evaluation. However, polysomnography may have various limitations, such as cost, expertise required for measurement, and physical and psychological stress imposed on the examinee, which may narrow its applications to short term measurements on a small selection of patients. It may be unrealistic to use polysomnography for tracking long-term trends or for executing screenings on a large population, both of which are crucial for a further understanding of sleep.

Actigraphy has been proposed as a simpler alternative for quantifying sleep. To measure body movements through the night, actigraphy usually requires the examinee to wear a wristband shaped accelerometer. Actigraphy is easily administrable and non-invasive to the examinee, and the cost is low, which is favorable for a long-term use. However, Actigraphy may be unable to wake up a user pleasantly at a moment having a greatest satisfaction.

The disclosed systems and methods are directed to solve one or more problems set forth above and other problems.

BRIEF SUMMARY OF THE DISCLOSURE

One aspect of the present disclosure includes a method for optimized wake-up strategy via sleeping stage prediction with recurrent neural networks. The method comprises receiving a set of raw sensory data of a user's sleeping status; translating the set of raw sensory data into a plurality of sleeping stages of the user; saving the plurality of sleeping stages as a history of sleeping stages of the user; based on the raw sensory data, determining a current sleeping stage of the user; based on the current sleeping stage and history of sleeping stages of the user, predicting a plurality of future sleeping stages of the user in an upcoming interval; calculating a wakeup score of the current sleeping stage and a wakeup score of each future sleeping stage; determining an optimized sleeping stage for wake up based on the wakeup score through comparing the wakeup score of the current sleeping stage and the wakeup scores of the future sleeping stages; and triggering an alarm impulse to wake up the user at the optimized sleeping stage for wake up.

One aspect of the present disclosure includes a non-transitory computer-readable medium having computer program for, when being executed by a processor, performing a method for a system for optimized wake-up strategy via sleeping stage prediction with recurrent neural networks based on multimodal deep neural network. The method comprises receiving a set of raw sensory data of a user's sleeping status; translating the set of raw sensory data into a plurality of sleeping stages of the user; saving the plurality of sleeping stages as a history of sleeping stages of the user; based on the raw sensory data, determining a current sleeping stage of the user; based on the current sleeping stage and history of sleeping stages of the user, predicting a plurality of future sleeping stages of the user in an upcoming interval; calculating a wakeup score of the current sleeping stage and a wakeup score of each future sleeping stage; determining an optimized sleeping stage for wake up based on the wakeup score through comparing the wakeup score of the current sleeping stage and the wakeup scores of the future sleeping stages; and triggering an alarm impulse to wake up the user at the optimized sleeping stage for wake up.

One aspect of the present disclosure includes a system for optimized wake-up strategy via sleeping stage prediction with recurrent neural networks. The system comprises a sleeping stage detection (SSD) module configured to receive a set of raw sensory data of a user's sleeping status, translate the set of raw sensory data into a plurality of sleeping stages of the user, save the plurality of sleeping stages as a history of sleeping stages of the user, and determine a current sleeping stage of the user based on the raw sensory data; a sleeping stage prediction (SSP) module configured to, based on the current sleeping stage and history of sleeping stages of the user, predict a plurality of future sleeping stages of the user in an upcoming interval; a wakeup score evaluation module configured to calculate a wakeup score of the current sleeping stage and a wakeup score of each future sleeping stage; a decision making module configured to compare the wakeup score of the current sleeping stage and the wakeup scores of the future sleeping stages and determine an optimized sleeping stage for wake up based on the wakeup score; and a wakeup module configured to trigger an alarm impulse to wake up the user at the optimized sleeping stage for wake up.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the invention, which are illustrated in the accompanying drawings. Hereinafter, embodiments consistent with the disclosure will be described with reference to drawings. Wherever possible, the same reference numbers will be used throughout the drawings to refer to the same or like parts. It is apparent that the described embodiments are some but not all of the embodiments of the present invention. Based on the disclosed embodiments, persons of ordinary skill in the art may derive other embodiments consistent with the present disclosure, all of which are within the scope of the present invention.

Figure 3:
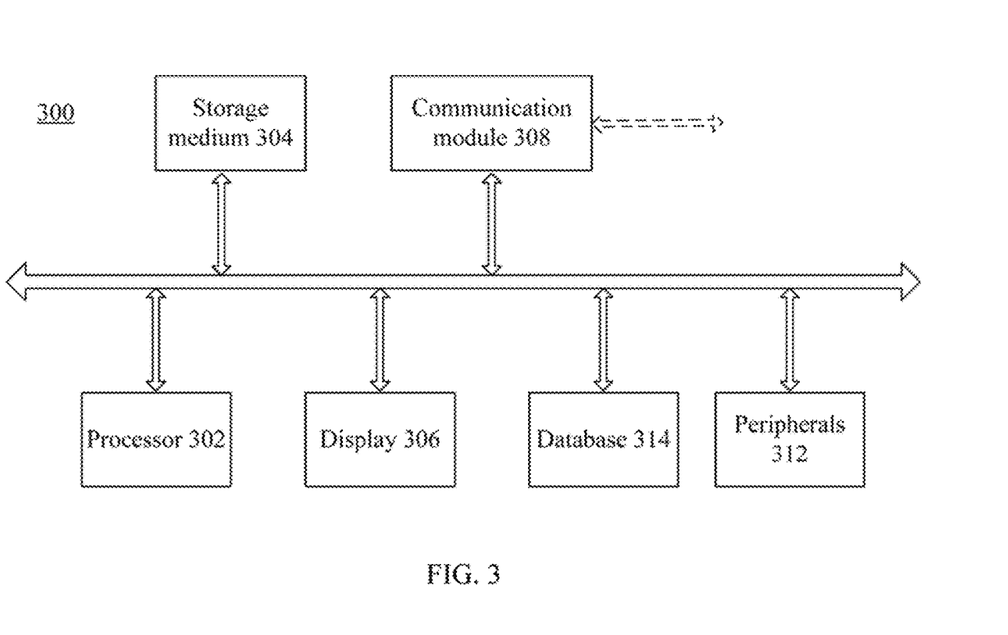
FIG. 3 illustrates an exemplary computing system consistent with disclosed embodiments.

As discussed above, people often experience two different phases of sleeps during the night: Rapid Eye Movement (REM) sleep and non-REM sleep, which may alternately appear through the night. The periodical rhythm of the REM and the non-REM sleeps are called a sleep cycle. Non-REM sleep can be subdivided into 4 sub-stages, in which each successive stage of non-REM sleep is indicative of a deeper sleep, with stage 1 as the lightest and stage 4 as the deepest. FIG. 3 illustrates a typical person's sleeping stages through the night. Certain studies indicate that people feel more comfortable when they wake up in the REM sleep than in the non-REM sleep. However, certain other studies indicate that the first non-REM sleeping-stage is the ideal stage for waking people up.

The present disclosure provides a system for optimized wake-up strategy via sleeping stage prediction with recurrent neural networks, which may wake up the user between REM and the first sleeping stage, such that the user may feel energized instead of dispirited upon awakening. In particular, each sleeping stage may be provided by a wakeup score, and an optimized sleeping stage for wake up may be determined based on the wakeup score through comparing the wakeup score of the current sleeping stage and the wakeup scores of the future sleeping stages.

Figure 2:
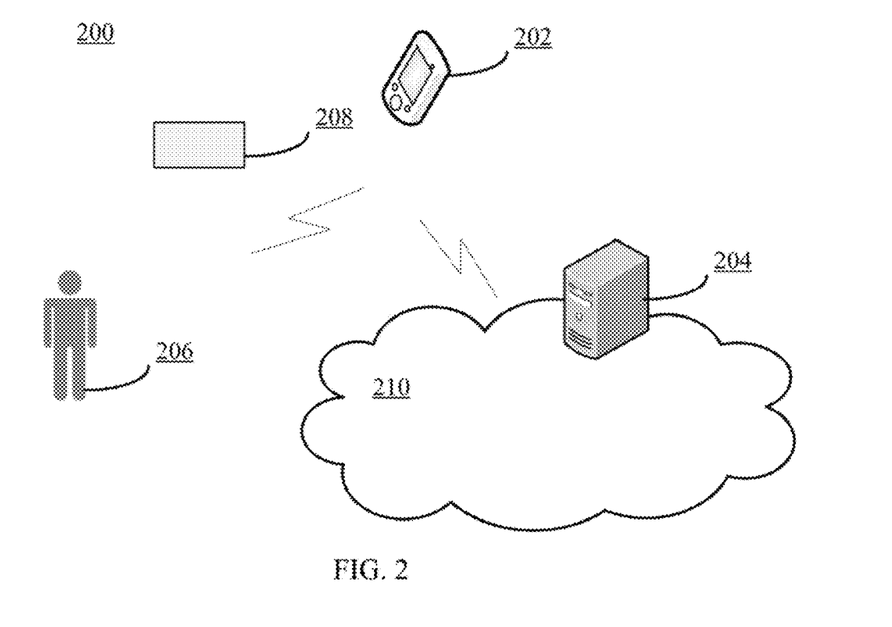
FIG. 2 illustrates an exemplary environment incorporating certain embodiments of the present invention.

FIG. 2 illustrates an exemplary environment 200 incorporating certain embodiments of the present invention. As shown in FIG. 1, the environment 200 may include a user terminal 202, a server 204, a user 206, a sensor 208, and a network 120. Other devices may also be included.

The user terminal 202 may include any appropriate type of electronic device with computing capabilities, such as a wearable device (e.g., a smart watch, a wristband), a mobile phone, a smartphone, a tablet, a personal computer (PC), a server computer, a laptop computer, and a digital personal assistant (PDA), etc.

The server 204 may include any appropriate type of server computer or a plurality of server computers for providing personalized contents to the user 206. For example, the server 204 may be a cloud computing server. The server 204 may also facilitate the communication, data storage, and data processing between the other servers and the user terminal 202. The user terminal 202, and server 204 may communicate with each other through one or more communication networks 120, such as cable network, phone network, and/or satellite network, etc.

The user 206 may interact with the user terminal 202 to query and to retrieve various contents and perform other activities of interest, or the user may use voice, hand or body gestures to control the user terminal 202 if speech recognition engines, motion sensor or depth-camera is used by the user terminal 202. The user 206 may be a single user or a plurality of users, such as family members.

The sensor 208 may be an internal sensor of the user terminal 202 and/or server 204, or may be an external sensor connected to the user terminal 202 and/or server 204 over the network 120. The sensor 208 may be a wearable band capable of tracking user's body movements in the bed, recording information of vital body functions like breathing, heartbeat through the night. The sensor 208 may also be a camera capable of monitoring user's body movements and providing physical body positions of the user. Further, the sensor 208 may be any appropriate type of sensors capable of tracking user's sleeping status through various ways, i.e., a sleeping status tracking sensor.

The user terminal 202, and/or server 204 may be implemented on any appropriate computing circuitry platform. FIG. 2 shows a block diagram of an exemplary computing system capable of implementing the user terminal 202, and/or server 204.

As shown in FIG. 3, the computing system 300 may include a processor 302, a storage medium 304, a display 306, a communication module 308, a database 314, and peripherals 312. Certain components may be omitted and other components may be added.

The processor 302 may include any appropriate processor or processors. Further, the processor 302 can include multiple cores for multi-thread or parallel processing. The storage medium 304 may include memory modules, such as ROM, RAM, flash memory modules, and mass storages, such as CD-ROM and hard disk, etc. The storage medium 304 may store computer programs for implementing various processes, when the computer programs are executed by the processor 302.

Further, the peripherals 312 may include various sensors and other I/O devices, such as keyboard and mouse, and the communication module 308 may include certain network interface devices for establishing connections through communication networks. The database 314 may include one or more databases for storing certain data and for performing certain operations on the stored data, such as database searching.

Figure 4:
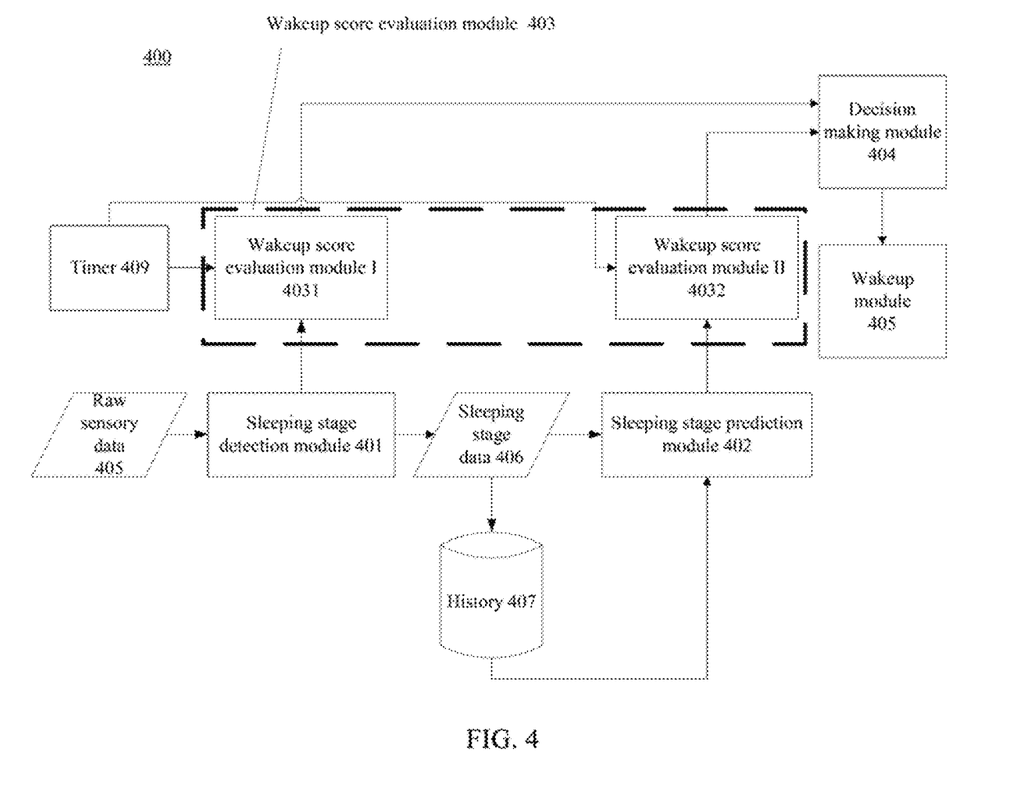
FIG. 4 illustrates an exemplary system for optimized wake-up strategy via sleeping stage prediction with recurrent neural networks consistent with disclosed embodiments.

FIG. 4 illustrates an exemplary system for optimized wake-up strategy via sleeping stage prediction with recurrent neural networks. As shown in FIG. 4, the system for optimized wake-up strategy via sleeping stage prediction with recurrent neural networks 400 may include a sleeping stage detection (SSD) module 401, a sleeping stage prediction (SSP) module 402, a wakeup score evaluation module 403, a decision making module 404, and a wakeup module 405.

The sleeping stage detection (SSD) module 401 may be configured to receive a set of raw sensory data, and translate the raw sensory data 405 (e.g., body movement or cardio-respiratory) into a plurality of sleeping stages or sleeping stage data. The sleeping stage detection (SSD) module 401 may also be called as a sleeping stage classification module. In one embodiment, the sleeping stage detection (SSD) module 401 may be configured to translate raw sensory data 405 (e.g., body movement or cardiorespiratory) into the sleeping stage data, according to a principle that each sleeping stage may have its unique pattern.

For example, as discussed above, FIG. 1 illustrates typical raw sensory data and corresponding sleeping stages, and the SSD module 401 may be to configured recognize a given pattern of sensory data and classify the pattern into pre-defined categories/classes of sleeping stages. The sleeping stage detection (SSD) module 401 may detect reliable sleeping stages with minor noise or generate a false detection result, which may be fed into the sleeping stage prediction (SSP) module 402.

For the translated plurality of sleeping stages or sleeping stage data, a current sleeping stage or current sleeping stage data 406 may be detected. On the other hand, the plurality of sleeping stages or sleeping stage data, for example, detected in the past several days, several months or even years, may be saved as historical sleeping stage data or history of detected sleeping stage data 407 for future training, analysis, etc. The history of detected sleeping stage data 407 may be saved in the system server. For example, the history of detected sleeping stage data 407 of the user may be recorded and stored in the cloud, and may be further analyzed through learning the correlations within the historical sleeping stage data 407 using machine learning techniques.

Based on the history of detected sleeping stage data 407 and the detected current sleeping stage data 406, the sleeping stage prediction (SSP) module 402 may be configured to predict a future sleeping stage of the user in an upcoming interval. In one embodiment, the sleeping stage prediction (SSP) module 402 may be configured to predict a future sleeping stage of the user in an upcoming interval, based on Recurrent Neural Networks (RNN) with a Long Short Term Memory (LSTM) model. The historical sleeping stage data 407 collected from users may be adopted for a training of LSTM. The sleeping stage prediction (SSP) module 402 may be configured to predict a future sleeping stage of the user based on the historical sleeping stage data 407 and the current sleeping stage data 406.

The wakeup score evaluation module 403 may be configured to obtain a wakeup score of the sleeping stage of the user based on a wakeup satisfaction of the sleeping stage of the user and a potential risk of waiting for the sleeping stage to come. To leverage the satisfaction and the risk, the wakeup score may be a fitness function to represent the wake-up righteousness. The wakeup satisfaction of the sleeping stage may refer to a degree of wakeup satisfaction when the user wakes up at a certain sleeping stage, and the potential risk of waiting for the certain sleeping stage to come may correspond to remaining wake-up intervals or remaining time before a so-called must-wakeup deadline detected by a timer 409. In certain embodiments, the wakeup score may be correlated with the wakeup satisfaction and the potential risk.

The wakeup score evaluation module 403 may further include a wakeup score evaluation module I 4031 and a wakeup score evaluation module II 4032. The wakeup score evaluation module I 4031 may be configured to calculate a wakeup score of the detected current sleeping stage of the user based on a wakeup satisfaction of the current sleeping stage of the user and a potential risk of waiting for the future sleeping stage to come. The wakeup score evaluation module II 4032 may be configured to calculate a wakeup score of the predicted future sleeping stage of the user based on a wakeup satisfaction of the future sleeping stage of the user and a potential risk of waiting for the future sleeping stage to come.

Based on the result of the sleeping stage prediction (SSD) module 401, the result of the sleeping stage prediction (SSP) module 402, and the remaining wake-up intervals detected by the timer 409, the decision making module 404 may be configured to make an optimized decision for awakening, i.e., when to wake up the user, based on the wakeup score. That is, the inputs of the decision making module 404 may include the detected current sleeping stage, the predicted sleeping stage in the approaching time interval, and the remaining time before the so-called must-wakeup deadline. The outputs of the decision making module 404 may include the optimized fitness score and the corresponding strategy. Thus, whether to wake up the user immediately or waiting for the moment (i.e., the optimum stage among the predicted stages) may be determined by the decision making module 404.

While evaluating the fitness score for two choices respectively, i.e., waking up the user immediately or waking up the user in the optimum stage among the predicted stages, the choice may be selected every minute (or other unit of time for each sleeping stage update) based on new sleeping stage detections and new sleeping stage predictions.

The wakeup module 405 may be configured to receive the decision made by the decision making module 404, and to wake up the user at the moment decided by the decision making module 404 through triggering an alarm impulse, e.g., a sound alarm, a vibration alarm, and a combination of sound alarm and vibration alarm, etc.

In particular, the wakeup score evaluation module I 4031 and the wakeup score evaluation module II 4032 may be configured to measure a wakeup satisfaction of the current sleeping stage and a wakeup satisfaction of the future sleeping stage first. The wakeup satisfaction of the current sleeping stage may refer to a degree of wakeup satisfaction when the user wakes up at the current sleeping stage. The wakeup satisfaction of the future sleeping stage may refer to a degree of wakeup satisfaction when the user wakes up at the future sleeping stage.

Figure 5:
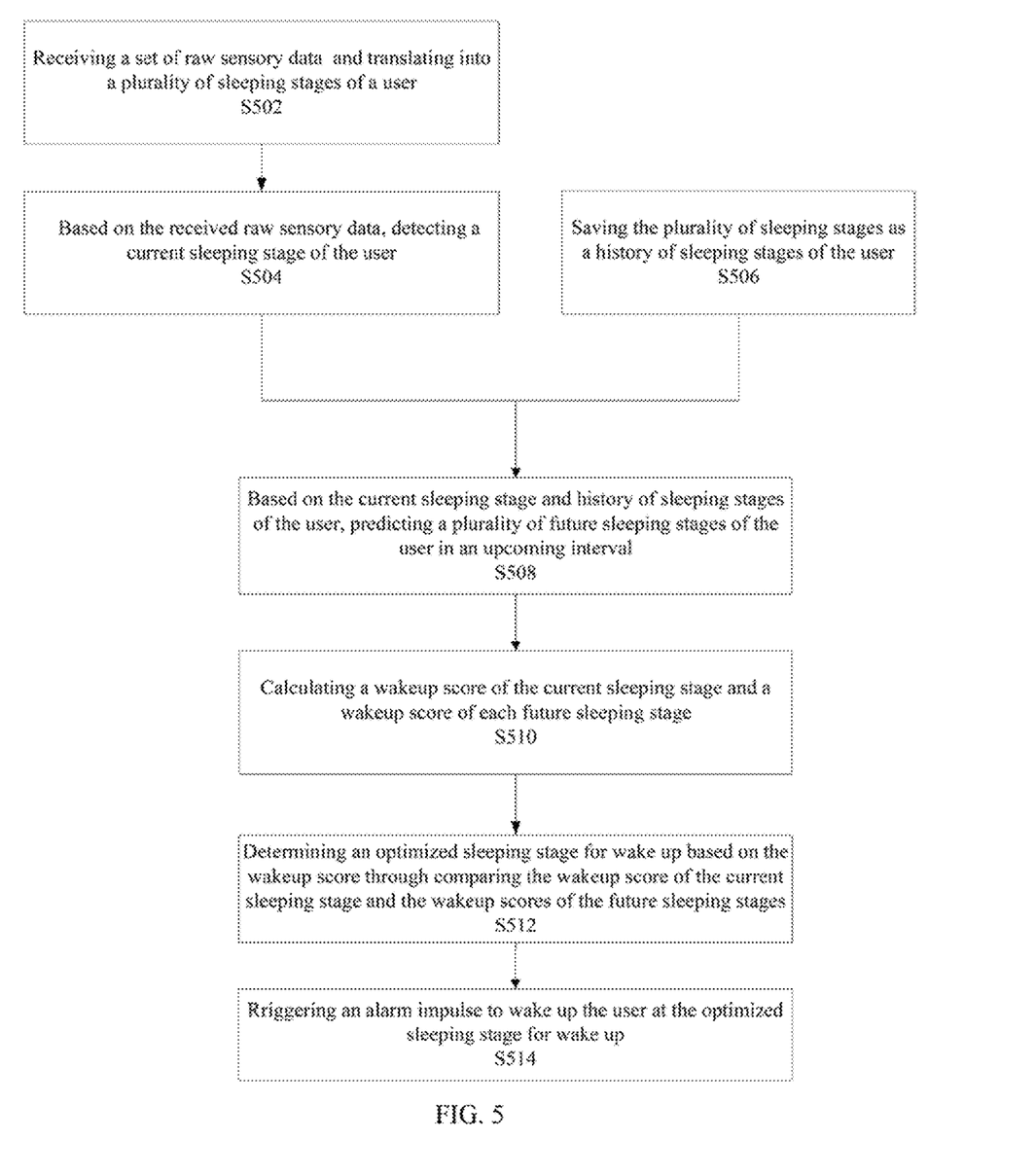
FIG. 5 illustrates a flow chart of an exemplary method for optimized wake-up strategy via sleeping stage prediction with recurrent neural networks consistent with disclosed embodiments.

The present disclosure also provides a method for a system for optimized wake-up strategy via sleeping stage prediction with recurrent neural networks. FIG. 5 illustrates a flow chart of an exemplary method for optimized wake-up strategy via sleeping stage prediction with recurrent neural networks consistent with disclosed embodiments.

As shown in FIG. 5, at the beginning, a set of raw sensory data (movement or cardiorespiratory) is received and is translated into a plurality of sleeping stages of a user (S502).

In particular, the raw sensory data may be provided by, for example, a smart phone, a wearable wristband, etc., which are capable of sensing the user's body movement in bed and/or cardiorespiratory. The raw sensory data (movement or cardiorespiratory) may be translated into the current sleeping stages of the user in various ways, all of which may be based on a principle that each sleeping stage has its unique pattern.

The step S502 may also be identified as a sleeping stage classification step. For example, in step S502, a given pattern of sensory data is recognized and the pattern is classified into pre-defined categories/classes of sleeping stages. The classification of the sleeping stage of the user may be considered as a pattern classification problem, and a generative model may be adopted to solve the pattern classification problem.

Further, based on the received raw sensory data (movement or cardiorespiratory) of a current sleeping moment, a current sleeping stage of the user is detected (S504).

Meanwhile, the plurality of sleeping stages of the user are saved as historical sleeping stage data or history of detected sleeping stage data for future training, analysis, etc. (S506).

The history of detected sleeping stage data may be saved in the system server. For example, the sleeping stage history of the user may be recorded and stored in the cloud, and may be further analyzed through learning the correlations within the historical sleeping stage data using machine learning techniques.

Based on the current sleeping stage of the user and the history of detected sleeping stage, a plurality of future sleeping stages of the user in an upcoming interval is predicted (S508). For example, every 30 minutes may be determined as a unit interval, in which the sleeping stage of the user may be predicted once a minute. Thus, 30 future sleeping stages may be predicted for the 30-minute-interval.

The prediction of the future sleeping stages of the user may be considered as a regression problem, and a discriminative model may be adopted to solve the regression problem. In one embodiment, the future sleeping stage of the user in the upcoming interval may be predicted, based on Recurrent Neural Networks (RNN) with a Long Short Term Memory (LSTM) model.

Traditional classification methods that employ spatiotemporal information usually involve computing multiple statistical functions over fixed number of time windows. Based on this, a static classifier such as support vector machines (SVM) will then be used to assign the predicted classes. The LSTM RNNs adopted in the disclosed embodiments may provide an alternative to the static classifier by dynamic classification, where the number of time windows is not fixed. Such a dynamic classification may not be achieved by traditional RNNs. Because the conventional RNNs cannot access long-range context due to the back-propagated error either inflating or decaying over time, which is called a vanishing gradient problem. By contrast, LSTM RNNs may overcome the vanishing gradient problem, and may be able to model a self-learned amount of context information.

Figure 6:
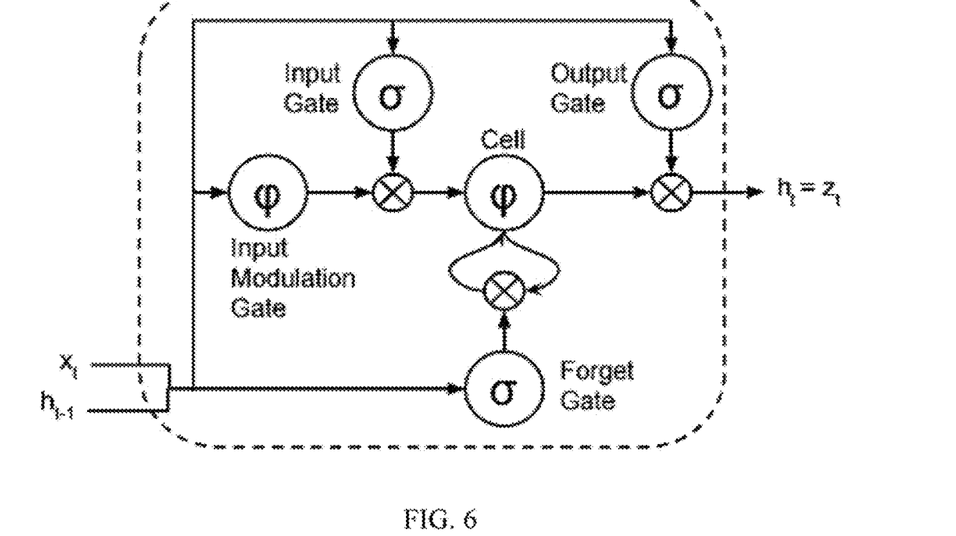
FIG. 6 illustrates an exemplary Long Short Term Memory (LSTM) unit consistent with disclosed embodiments.

FIG. 6 illustrates an exemplary Long Short Term Memory (LSTM) unit consistent with disclosed embodiments. As shown in FIG. 6, different from standard RNNs, the LSTM architecture may use memory cells to store and output information, allowing a better discovery of long-range temporal relations. Let $\sigma=(1+e^{-x})^{-1}$ denote a sigmoid nonlinearity which squashes real-valued inputs to a [0, 1] range, where $$\phi(x) = \frac{e^x - e^x}{e^x + e^x},$$

LSTM updates for timestamp t given inputs $x_t$, $h_{t-1}$, and $c_{t-1}$ are written as:

$$i_t = \sigma(W_{xi}x_t + W_{hi}h_{t-1} + b_i) \quad (1)$$

$$f_t = \sigma(W_{xf}x_t + W_{hf}h_{t-1} + b_f) \quad (2)$$

$$o_t = \sigma(W_{xo}x_t + W_{ho}h_{t-1} + b_o) \quad (3)$$

$$g_t = \sigma(W_{xc}x_t + W_{hc}h_{t-1} + b_c) \quad (4)$$

$$h_t = o_t \odot \phi(c_t) \quad (5)$$

Figure 7:
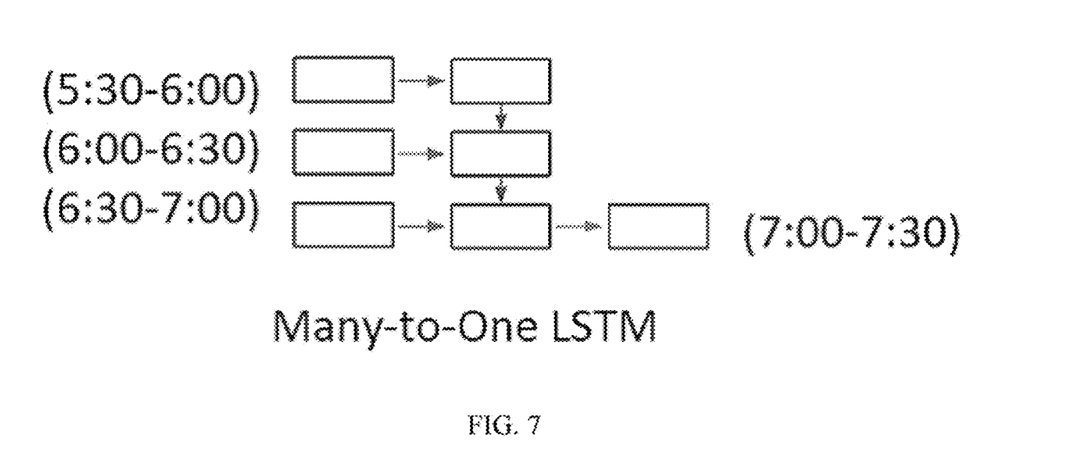
FIG. 7 illustrates an exemplary many-to-one LSTM for sleeping stage (sequence signal) prediction consistent with disclosed embodiments.

LSTM is capable of sequence processing, as well as long-range context learning. For sleeping stages, the data may be long-ranged. For example, every 30 minutes may be determined as a unit period, in which the sleeping stage may change several times. FIG. 7 illustrates an exemplary many-to-one LSTM for sleeping stage (sequence signal) prediction consistent with disclosed embodiments. As shown in FIG. 7, the sleeping stage of the user may be predicted with LSTM once a minute, and the predicted sleeping stages may be updated accordingly. In this way, a 30-minute pool of future sleeping stage predictions may be obtained.

Historical sleeping stage data collected from users may be adopted for a training of LSTM. For example, a 90-minute pool of sleeping stage data may be selected as LSTM input, and the following 30-minute pool of sleeping stage data may be used as the ground truth. The LSTM may learn the generalized patterns when trained with large amounts of data. In particular, the sleeping stage data may be quantized and flattened as a 30 dimensional vector for each unit. The LSTM may be fed with a series of units for one prediction. In one embodiment, as shown in FIG. 7, 3 units of sleeping stage data, i.e., sleeping stage data of 5:30-6:00, 6:00-6:30, and 6:30-7:00, may be used to predict the upcoming unit of sleeping stages, i.e., sleeping stage data of 7:00-7:30, which may be represented by another vector of length 30.

Mean Squared Error (MSE) may be adopted for training LSTM:

$$L_{MSE} = \frac{1}{n}\sum_{i=1}^{n} \|V_{target} - V_{pred}\|_2^2 \quad (6)$$

where $V_{pred}$ denotes a predicted vector, $V_{target}$ denotes the ground truth denoted, and $\|\cdot\|$ denotes the squared Euclidean norm. The Adam method may be adopted for stochastic optimization.

After the current sleeping stage is detected and the plurality of future sleeping stages of the user in the upcoming interval are predicted, wakeup scores for the current sleeping stage and each future sleeping stage is calculated (S510).

Given an online sequence of sleeping stages, the sleeping stages in the next time slot may be predicted. The disclosed method may wake up the user pleasantly at a moment having a greatest corresponding satisfaction. However, the prediction of the sleeping stage may be different from actual observations of the user's sleeping stage to a certain extent. Thus, the strategies of the disclosed system are desired to be adjusted.

In particular, the prediction of the sleeping stage may diverge from the real sleeping stage for several reasons. For example, the data may not be sufficient for the neural network to learn an adequately generalized model; the inherent sleeping pattern of a user may change over time, due to age and daily behaviors; the previous sleeping stage detection procedure may inevitably involve noise, which is transferred to the next procedure of sleeping stage prediction; during sleeping, other external factors may affect the user's sleeping quality, e.g., sudden noise, lighting condition changes, etc.

Thus, based on the result of the sleeping stage prediction, the current detected sleeping stage, and the budget of remaining wake-up intervals, a scheme to decide when to wake up the user is highly desired. If erroneous prediction is made, more remaining time may indicate more opportunities for a successful future wake-up call, while less time may indicate a higher degree of urgency.

To leverage the satisfaction and the risk, a fitness function to represent the wake-up righteousness, called a wakeup score, may be provided. The wakeup score denoted by $S_w$ is written as:

$$S_w = f_w(s,t) \quad (7)$$

where s denotes a sleeping stage to be evaluated, and t denotes a time interval between the sleeping stage to be evaluated and a wake-up deadline. Further, the wakeup score $S_w$ of a certain sleeping stage may be correlated with a wakeup satisfaction $S_a$ of the certain sleeping stage and a potential risk of waiting for the certain sleeping stage to come (which may not). The potential risk may be indicated by an urgency factor denoted by U:

$$U = f_u(s,t) \quad (8)$$

The wakeup satisfaction of the current sleeping stage may refer to a degree of wakeup satisfaction when the user wakes up at the current sleeping stage. The wakeup satisfaction of the future sleeping stage may refer to a degree of wakeup satisfaction when the user wakes up at the future sleeping stage.

To measure the wake-up satisfaction, a mapping relationship between a wake-up stage and a corresponding satisfaction value may be built. The mapping may be empirically defined, where the REM and the first sleeping stages earn the most credit. $S_a$ denotes a wakeup satisfaction, which is a generic function of s and t, is written as:

$$S_a = f_s(s,t) \quad (9)$$

Thus, the correlation between the wakeup score $S_w$ and the wakeup satisfaction $S_a$ is formulized as:

$$f_w(s,t) = f_s(s,t) \times (1 - f_u(s,t)) \quad (10)$$

Figure 8:
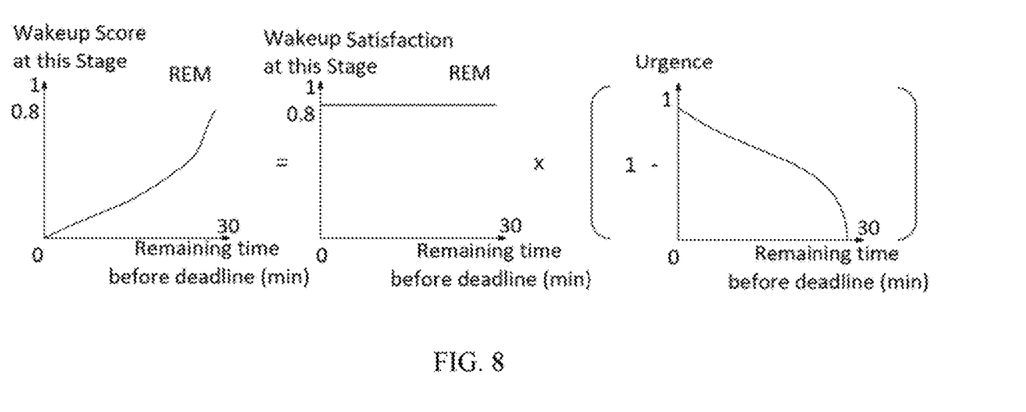
FIG. 8 illustrates an exemplary wakeup score for REM Sleeping Stage consistent with disclosed embodiments.

FIG. 8 illustrates an exemplary wakeup score for REM Sleeping Stage consistent with disclosed embodiments. As shown in FIG. 8, the wakeup score function $f_w(s,t)$ for each sleeping stage may be derived based on the satisfaction functions $f_s(s,t)$ and the urgency function $f_u(s,t)$. If erroneous prediction is unfortunately made, more remaining time may indicate more opportunities for a successful future wake-up call, while less time may indicate a higher degree of urgency In particular, the wakeup score for each sleeping stage may be derived empirically by defining the corresponding wakeup satisfaction and urgency factor. Other sleeping stages (e.g., non-REM sleeping stages) may have distinct satisfaction functions $f_s(s,t)$ but usually share the same urgency function $f_u(s,t)$.

After the wakeup score for each sleeping stage is calculated, an optimized decision for awakening or waking up the user is made (S512). In particular, the decision making module may make the optimized decision for awakening through adopting an optimization approach to decide when to wake up the user based on the wakeup score.

The input of the decision making module may be the detected current sleeping stage, the predicted sleeping stage in the approaching time interval, and the remaining time before the so-called must-wakeup deadline. The output of the decision making module, may be the optimized fitness score and the corresponding wake up strategy, thus, whether to wake up the user immediately or waiting for the moment (i.e., the optimum stage among the predicted stages) may be determined. The moment having the optimized fitness score is called as an optimized sleeping stage for waking up.

While evaluating the fitness score for two choices respectively, i.e., waking up the user immediately and waking up the user in the optimum stage among the predicted stages, the choice may be selected every minute (or other unit of time for each sleeping stage update) based on new sleeping stage detections and new sleeping stage predictions.

The optimized fitness score, denoted as $L_{fitness}$, is written as $$L_{fitness} = F(f'_w(s',t_c), \max_{s \in S}(f_w(s,t_s))) \quad (11)$$

where $f'_w(s',t_c)$ denotes the wakeup score of the current sleep stage s' at current time $t_c$, which is detected in the SSD stage, i.e., S502. $f_w(s, t_s)$ denotes the wakeup score in a sleeping stage s at its corresponding time $t_s$, which is predicted in the SSP stage, i.e., S504. Thus, the best strategy by maximizing $L_{fitness}$ may be realized in the decision making stage, i.e., S510.

The strategy or the criterion F may be generic and may be replaced. In the disclosed embodiment, the strategy or the criterion F may be a max function to pick the greater side while leveraging the current detection and future prediction. In another embodiment, one side may be given a greater weight emphasize certainty over opportunity cost, or in the language of product, the satisfactoriness may be given less credit to be less offensive.

After the optimized decision for waking up the user is made, an alarm impulse is triggered to wake up the user at the decided optimized wakeup moment (S514). The alarm impulse may be a sound alarm, a vibration alarm, and a combination of sound alarm and vibration alarm, etc.

Sleep is a very important part of human's daily life, and sleep quality has a great impact on various aspects of one's metal and physical status, such as one's fatigue, mood, attention, and concentration, etc. The disclosed system and method for optimized wake-up strategy via sleeping stage prediction with recurrent neural networks may wake up the user between REM sleeping stage and the first sleeping stage, in which the user may feel energized rather than dispirited upon awakening. Recurrent neural networks may be adopted for the sleeping stage prediction (SSP) module. Based on the results generated by the sleeping stage prediction (SSP) module and the results generated by the sleeping stage detection (SSD) module, an optimized wake-up strategy may be determined.

By empirically assigning a fitness function for each sleeping stage, which denotes the wakeup score over the remaining wake-up period of time, the decision making module may evaluate the comfort of the corresponding sleeping stage in conjunction with the urgency of the corresponding sleeping stage to come. Thus, the disclosed system may not only take advantage brought by the sleeping stage prediction (SSP) module, but also embrace uncertainty and evade high opportunity cost by false predictions.

Those of skill would further appreciate that the various illustrative modules and method steps disclosed in the embodiments may be implemented as electronic hardware, computer software, or combinations of both. To clearly illustrate this interchangeability of hardware and software, various illustrative units and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The description of the disclosed embodiments is provided to illustrate the present invention to those skilled in the art. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for optimized wake-up strategy via sleeping stage prediction with recurrent neural networks, comprising:
   receiving a set of raw sensory data of a user's sleeping status;
   translating the set of raw sensory data into a plurality of sleeping stages of the user;
   saving the plurality of sleeping stages as a history of sleeping stages of the user;
   based on the raw sensory data, determining a current sleeping stage of the user;
   based on the current sleeping stage and history of sleeping stages of the user, predicting a plurality of future sleeping stages of the user in an upcoming interval;
   calculating a wakeup score of the current sleeping stage and a wakeup score of each future sleeping stage;
   determining an optimized sleeping stage for wake up based on the wakeup score through comparing the wakeup score of the current sleeping stage and the wakeup scores of the future sleeping stages; and
   triggering an alarm impulse to wake up the user at the optimized sleeping stage for wake up.

2. The method for optimized wake-up strategy via sleeping stage prediction with recurrent neural networks according to claim 1, wherein translating the set of raw sensory data into a plurality of sleeping stages of the user further including:
   recognizing a pattern of the raw sensory data and classify the pattern into pre-defined categories/classes of sleeping stages.

3. The method for optimized wake-up strategy via sleeping stage prediction with recurrent neural networks according to claim 1, wherein:
   the raw sensory data of the user's sleeping status includes at least one of the user's body movement data and cardiorespiratory data during a sleep.

4. The method for optimized wake-up strategy via sleeping stage prediction with recurrent neural networks according to claim 1, wherein predicting a plurality of future sleeping stages of the user in an upcoming interval includes:
   predicting the plurality of future sleeping stages of the user in the upcoming interval based on Recurrent Neural Networks (RNN) with a Long Short Term Memory (LSTM) model, wherein $\sigma=(1+e^{-x})^{-1}$ denotes a sigmoid nonlinearity which squashes real-valued inputs to a $[0, 1]$ range, where $$\phi(x) = \frac{e^x - e^x}{e^x + e^x},$$

and LSTM updates for timestamp t given inputs $x_t$, $h_{t-1}$, and $c_{t-1}$ are written as:

$$i_t = \sigma(W_{xi}x_t + W_{hi}h_{t-1} + b_i)$$

$$f_t = \sigma(W_{xf}x_t + W_{hf}h_{t-1} + b_f)$$

$$o_t = \sigma(W_{xo}x_t + W_{ho}h_{t-1} + b_o)$$

$$g_t = \sigma(W_{xc}x_t + W_{hc}h_{t-1} + b_c)$$

$$h_t = o_t \odot \phi(c_t)$$

5. The method for optimized wake-up strategy via sleeping stage prediction with recurrent neural networks according to claim 1, wherein calculating a wakeup score of the current sleeping stage and a wakeup score of each future sleeping stage further including:
   correlating the wakeup score of the sleeping stage with a wakeup satisfaction of a corresponding sleeping stage and a potential risk of waiting the corresponding sleeping stage to come.

6. The method for optimized wake-up strategy via sleeping stage prediction with recurrent neural networks according to claim 5, wherein:
   a correlation between the wakeup score $S_w$ and the wakeup satisfaction $S_a$ is $$f_w(s,t) = f_s(s,t) \times (1 - f_u(s,t)),$$

where $S_w$ denotes the wakeup score, $S_w = f_w(s, t)$, s denotes a sleeping stage to be evaluated, t denotes a time interval between the sleeping stage to be evaluated and a wake-up deadline, $f_w(s, t)$ is a wakeup score function, U denotes the potential risk of waiting the sleeping stage to come, $U = f_u(s, t)$, $f_u(s, t)$ is an urgency function, and $S_a$ denotes the wakeup satisfaction, $S_a = f_s(s, t)$, $f_s(s, t)$ is a satisfaction function.

7. The method for optimized wake-up strategy via sleeping stage prediction with recurrent neural networks according to claim 1, wherein determining an optimized sleeping stage for wake up based on the wakeup score through comparing the wakeup score of the current sleeping stage and the wakeup scores of the future sleeping stages further including:
   determining the optimized sleeping stage for wake up having an optimized fitness score, wherein the optimized fitness score denoted as $L_{fitness}$, is written as $$L_{fitness} = F(f'_w(s', t_c), \max_{s \in S}(f_w(s, t_s)))$$

where $f'_w(s', t_c)$ denotes the wakeup score of the current sleeping stage s' at current time $t_c$, $f_w(s, t_s)$ denotes the wakeup score of the future sleeping stage s at its corresponding time $t_s$, S denotes the plurality of future sleeping stages, and F denotes a wakeup strategy or a wakeup criterion.

8. The method for optimized wake-up strategy via sleeping stage prediction with recurrent neural networks according to claim 6, wherein:
   the wakeup strategy F is a max function to select a sleeping stage having a largest wakeup score from the current sleeping stage and the plurality of future sleeping stages.

9. A non-transitory computer-readable medium having computer program for, when being executed by a processor, performing a method for a system for optimized wake-up strategy via sleeping stage prediction with recurrent neural networks based on multimodal deep neural network, the method comprising:
   receiving a set of raw sensory data of a user's sleeping status;
   translating the set of raw sensory data into a plurality of sleeping stages of the user;

saving the plurality of sleeping stages as a history of sleeping stages of the user;
based on the raw sensory data, determining a current sleeping stage of the user;
based on the current sleeping stage and history of sleeping stages of the user, predicting a plurality of future sleeping stages of the user in an upcoming interval;
calculating a wakeup score of the current sleeping stage and a wakeup score of each future sleeping stage;
comparing the wakeup score of the current sleeping stage and the wakeup scores of the future sleeping stages, determining an optimized sleeping stage for wake up based on the wakeup score; and
triggering an alarm impulse to wake up the user at the optimized sleeping stage for wake up.

10. The non-transitory computer-readable medium according to claim 9, wherein translating the set of raw sensory data into a plurality of sleeping stages of the user further including:
recognizing a pattern of the raw sensory data and classify the pattern into pre-defined categories/classes of sleeping stages, wherein the raw sensory data of the user's sleeping status includes at least one of the user's body movement data and cardiorespiratory data during a sleep.

11. The non-transitory computer-readable medium according to claim 9, wherein predicting a plurality of future sleeping stages of the user in an upcoming interval includes:
predicting the plurality of future sleeping stages of the user in the upcoming interval based on Recurrent Neural Networks (RNN) with a Long Short Term Memory (LSTM) model, wherein $\sigma=(1+e^{-x})^{-1}$ denotes a sigmoid nonlinearity which squashes real-valued inputs to a [0, 1] range, where $$\phi(x) = \frac{e^x - e^x}{e^x + e^x},$$

and LSTM updates for timestamp t given inputs $x_t$, $h_{t-1}$, and $c_{t-1}$ are written as:

$$i_t = \sigma(W_{xi}x_t + W_{hi}h_{t-1} + b_i)$$

$$f_t = \sigma(W_{xf}x_t + W_{hf}h_{t-1} + b_f)$$

$$o_t = \sigma(W_{xo}x_t + W_{ho}h_{t-1} + b_o)$$

$$g_t = \sigma(W_{xc}x_t + W_{hc}h_{t-1} + b_c)$$

$$h_t = o_t \odot \phi(c_t)$$

12. The non-transitory computer-readable medium according to claim 9, wherein calculating a wakeup score of the current sleeping stage and a wakeup score of each future sleeping stage further including:
correlating the wakeup score of the sleeping stage with a wakeup satisfaction of the corresponding sleeping stage and a potential risk of waiting the corresponding sleeping stage to come, wherein a correlation between the wakeup score $S_w$ and the wakeup satisfaction $S_a$ is $$f_w(s,t) = f_s(s,t) \times (1 - f_u(s,t)),$$

where $S_w$ denotes the wakeup score, $S_w = f_w(s, t)$, s denotes a sleeping stage to be evaluated, t denotes a time interval between the sleeping stage to be evaluated and a wake-up deadline, $f_w(s, t)$ is a wakeup score function, U denotes the potential risk of waiting the sleeping stage to come, $U = f_u(s, t)$, $f_u(s, t)$ is an urgency function, and $S_a$ denotes the wakeup satisfaction, $S_a = f_s(s, t)$, $f_s(s, t)$ is a satisfaction function.

13. The non-transitory computer-readable medium according to claim 9, wherein determining an optimized sleeping stage for wake up based on the wakeup score through comparing the wakeup score of the current sleeping stage and the wakeup scores of the future sleeping stages further including:
determining the optimized sleeping stage for wake up having an optimized fitness score, wherein the optimized fitness score denoted as $L_{fitness}$, is written as $$L_{fitness} = F(f'_w(s',t_c), \max_{s \in S}(f_w(s,t_s)))$$

where $f'_w(s', t_c)$ denotes the wakeup score of the current sleeping stage s' at current time $t_c$, $f_w(s, t_s)$ denotes the wakeup score of the future sleeping stage s at its corresponding time $t_s$, S denotes the plurality of future sleeping stages, and F denotes a wakeup strategy or a wakeup criterion.

14. The non-transitory computer-readable medium according to claim 13, wherein:
the wakeup strategy F is a max function to select a sleeping stage having a largest wakeup score from the current sleeping stage and the plurality of future sleeping stages.

15. A system for optimized wake-up strategy via sleeping stage prediction with recurrent neural networks based on multimodal deep neural network, comprising:
a memory storing computer-executable instructions; and
a processor, when executing the computer-executable instructions, configured to:
receive a set of raw sensory data of a user's sleeping status, translate the set of raw sensory data into a plurality of sleeping stages of the user, save the plurality of sleeping stages as a history of sleeping stages of the user, and determine a current sleeping stage of the user based on the raw sensory data;
predict a plurality of future sleeping stages of the user in an upcoming interval based on the current sleeping stage and history of sleeping stages of the user;
calculate a wakeup score of the current sleeping stage and a wakeup score of each future sleeping stage;
compare the wakeup score of the current sleeping stage and the wakeup scores of the future sleeping stages and determine an optimized sleeping stage for wake up based on the wakeup score; and
trigger an alarm impulse to wake up the user at the optimized sleeping stage for wake up.

16. The system for optimized wake-up strategy via sleeping stage prediction with recurrent neural networks based on multimodal deep neural network according to claim 15, wherein the processor is further configured to:
recognize a pattern of the raw sensory data and classify the pattern into pre-defined categories/classes of sleeping stages, wherein the raw sensory data of the user's sleeping status includes at least one of the user's body movement data and cardiorespiratory data during a sleep.

17. The system for optimized wake-up strategy via sleeping stage prediction with recurrent neural networks based on multimodal deep neural network according to claim 15, wherein the processor is further configured to:
predict the plurality of future sleeping stages of the user in the upcoming interval based on Recurrent Neural Networks (RNN) with a Long Short Term Memory (LSTM) model, wherein $\sigma=(1+e^{-x})^{-1}$ denotes a sigmoid nonlinearity which squashes real-valued inputs to a [0, 1] range, where $$\phi(x) = \frac{e^x - e^x}{e^x + e^x},$$

and LSTM updates for timestamp t given inputs $x_t$, $h_{t-1}$, and $c_{t-1}$ are written as:

$$i_t = \sigma(W_{xi}x_t + W_{hi}h_{t-1} + b_i)$$

$$f_t = \sigma(W_{xf}x_t + W_{hf}h_{t-1} + b_f)$$

$$o_t = \sigma(W_{xo}x_t + W_{ho}h_{t-1} + b_o)$$

$$g_t = \sigma(W_{xc}x_t + W_{hc}h_{t-1} + b_c)$$

$$h_t = o_t \odot \phi(c_t)$$

18. The system for optimized wake-up strategy via sleeping stage prediction with recurrent neural networks based on multimodal deep neural network according to claim 15, wherein the processor is further configured to:
    correlate the wakeup score of the sleeping stage with a wakeup satisfaction of the corresponding sleeping stage and a potential risk of waiting the corresponding sleeping stage to come, wherein a correlation between the wakeup score $S_w$ and the wakeup satisfaction $S_a$ is $$f_w(s,t) = f_s(s,t) \times (1 - f_u(s,t)),$$

where $S_w$ denotes the wakeup score, $S_w = f_w(s, t)$, s denotes a sleeping stage to be evaluated, t denotes a time interval between the sleeping stage to be evaluated and a wake-up deadline, $f_w(s, t)$ is a wakeup score function, U denotes the potential risk of waiting the sleeping stage to come, $U = f_u(s, t)$, $f_u(s, t)$ is an urgency function, and $S_a$ denotes the wakeup satisfaction, $S_a = f_s(s, t)$, $f_s(s, t)$ is a satisfaction function.

19. The system for optimized wake-up strategy via sleeping stage prediction with recurrent neural networks based on multimodal deep neural network according to claim 15, wherein the processor is further configured to:
    determine the optimized sleeping stage for wake up having an optimized fitness score, wherein the optimized fitness score denoted as $L_{fitness}$, is written as $$L_{fitness} = F(f'_w(s', t_c), \max_{s \in S}(f_w(s, t_s)))$$

where $f'_w(s', t_c)$ denotes the wakeup score of the current sleeping stage s' at current time $t_c$, $t_w(s, t_s)$ denotes the wakeup score of the future sleeping stage s at its corresponding time $t_s$, S denotes the plurality of future sleeping stages, and F denotes a wakeup strategy or a wakeup criterion.

20. The system for optimized wake-up strategy via sleeping stage prediction with recurrent neural networks based on multimodal deep neural network according to claim 19, wherein:
    the wakeup strategy F is a max function to select a sleeping stage having a largest wakeup score from the current sleeping stage and the plurality of future sleeping stages.

* * * * *